(12) United States Patent
Slater et al.

(10) Patent No.: US 9,192,477 B2
(45) Date of Patent: Nov. 24, 2015

(54) ARTIFICIAL HIP JOINT STEM, STEM INSERTER, ARTIFICIAL HIP JOINT SYSTEM INCLUDING THEM, AND ARTIFICIAL HIP JOINT

(71) Applicant: KYOCERA Medical Corporation, Osaka-shi, Osaka (JP)

(72) Inventors: Nicholas Slater, Chandler, AZ (US); Jeffery D. Arnett, Gilbert, AZ (US); Joshua A. Butters, Chandler, AZ (US); Takatoshi Miyashita, Hirakata (JP); Noboru Kazumi, Ichikawa (JP); Takao Ida, Osaka (JP)

(73) Assignee: KYOCERA MEDICAL CORPORATION, Osaka (JP)

( * ) Notice: Subject to any disclaimer, the term of this patent is extended or adjusted under 35 U.S.C. 154(b) by 63 days.

(21) Appl. No.: 14/141,640

(22) Filed: Dec. 27, 2013

(65) Prior Publication Data
US 2015/0182341 A1 Jul. 2, 2015

(51) Int. Cl.
*A61F 2/36* (2006.01)
*A61F 2/32* (2006.01)

(52) U.S. Cl.
CPC ........................................ *A61F 2/32* (2013.01)

(58) Field of Classification Search
CPC ........... A61F 2/36; A61F 2/3607; A61F 2/46; A61F 2/4607; A61F 2/367; A61F 2002/4681
See application file for complete search history.

(56) References Cited

U.S. PATENT DOCUMENTS

| 6,626,913 B1* | 9/2003 | McKinnon et al. | 606/99 |
| 2009/0112209 A1* | 4/2009 | Parrott et al. | 606/62 |

OTHER PUBLICATIONS

Stryker Japan K.K.; "Accolade TMZF Cementless Hip System"; 2011 (Searched on Sep. 12, 2013); in Japanese; 4 pages online; 8 pages printed. URL: http://www.strykercom.jp/mpsite2/product/data/01-01/HE01-135.pdf.

* cited by examiner

*Primary Examiner* — Brian Dukert
(74) *Attorney, Agent, or Firm* — Volpe and Koenig, P.C.

(57) ABSTRACT

In an artificial hip joint stem of the present invention, a distance between an inner wall portion and an outer wall portion is decreased as separating from an opening part in a sectional view that is parallel to a stem central axis and includes the inner wall portion and the outer wall portion, and both a front wall portion and a rear wall portion have a planar region in a sectional view that is parallel to the stem central axis and includes the front wall portion and the rear wall portion. A stem inserter of the present invention includes a disk-shaped front end part. The present invention also provides an artificial hip joint system including the artificial hip joint stem and the stem inserter, and an artificial hip joint including the artificial hip joint stem.

16 Claims, 9 Drawing Sheets

ARTIFICIAL HIP JOINT STEM, STEM INSERTER, ARTIFICIAL HIP JOINT SYSTEM INCLUDING THEM, AND ARTIFICIAL HIP JOINT

TECHNICAL FIELD

The present invention relates to an artificial hip joint stem, a stem inserter, an artificial hip joint system including them, and an artificial hip joint.

BACKGROUND ART

In order to restore the function of a hip joint deteriorated by disease or injury due to an accident or the like, hip replacement arthroplasty for replacing the hip joint with an artificial hip joint has been carried out conventionally. An artificial hip joint stem (hereinafter generally referred to as "stem") among members constituting the artificial hip joint is the substantially rod-shaped curved member. The stem implanted into a medullary cavity of a thigh bone through the following steps (i) to (iii).

(i) The first step is to make incisions into skin and muscle and resect the head of the thigh bone.

(ii) The next step is to form a first hole serving as a stem shaft and a second hole having the same shape as the stem along the first hole in the medullary cavity of the resulting thigh bone.

(iii) The last step is to implant the stem into the medullary cavity of the thigh bone by driving the stem into the second hole.

The implantation of the stem in the step (iii) among the above steps (i) to (iii) is carried out using a substantially column-shaped stem inserter (hereinafter generally referred to as "inserter") (for example, refer to non patent document 1). That is, in the step (iii), the stem is implanted by attaching the inserter to the stem and then driving the stem into the second hole by striking a rear end part of the inserter with a hammer.

The non patent document 1 describes the configuration that a screw part located at the front end part of the inserter is screw fixed to a screw hole located in a shoulder part of the stem. Therefore, according to the configuration described in the non patent document 1, the substantially column-shaped inserter is screw fixed from the shoulder part of the stem along the longitudinal direction of the stem. Consequently, the driving of the stem is performed only from immediately above the stem. If the stem driving direction is limited to the direction from immediately above the stem, it may be difficult to drive the stem depending on surgical procedure. If the stem is subjected to forced driving from an oblique direction, the stem and the inserter may bite each other. Hence, there are several risks that it may be difficult to separate the stem and the inserter from each other and both may be damaged. This problem occurs notably with the surgical procedure performed in supine position (lying face up), such as direct anterior approach, in which the abdomen of a patient is liable to create an obstacle to the driving.

PRIOR ART

Non Patent Document

Non patent document 1: "Accolade TMZF Cementless Hip System," four pages, (online), 2011, Stryker Japan K.K. (searched on Sep. 12, 2013), Internet (URL: http://www/stryker.co.jp/mpsite2/product/data/01-01/HE01-135.pdf)

SUMMARY OF THE INVENTION

Problems to be Solved by Invention

An object of the present invention is to provide an artificial hip joint stem having excellent driving performance, a stem inserter, an artificial hip joint system including them, and an artificial hip joint.

Means for Solving the Problems

The artificial hip joint stem of the present invention includes a concave part located in a shoulder part of a stem body. The concave part includes an opening part that opens into the shoulder part, and a wall part extending along a stem central axis of the stem body. The wall part includes an inner wall portion and an outer wall portion opposed to each other, and a front wall portion and a rear wall portion opposed to each other. A distance between the inner wall portion and the outer wall portion is decreased as separating from the opening part in a sectional view that is parallel to the stem central axis and includes the inner wall portion and the outer wall portion. Both the front wall portion and the rear wall portion have a planar region in a sectional view that is parallel to the stem central axis and includes the front wall portion and the rear wall portion.

The stem inserter of the present invention includes a disk-shaped front end part.

The artificial hip joint system of the present invention includes the foregoing artificial hip join stem of the present invention and the foregoing stem inserter of the present invention. The stem inserter is housed in the concave part in a state that an upper surface and a lower surface of the front end part are respectively opposed to the front wall portion and the rear wall portion of the concave part, and in a state that the stem inserter is inclinable around an inserter central axis extending between the upper surface and the lower surface.

The artificial hip joint of the present invention includes: the artificial hip joint stem of the present invention which further includes a neck part extending from a proximal end of the stem body; an artificial bone head fitted into the neck part; and a socket for slidably housing the artificial bone head.

Effect of the Invention

The present invention produces an effect of being excellent in driving the stem.

BRIEF DESCRIPTION OF THE DRAWINGS

FIG. 1(*b*) is a partially enlarged view of FIG. 1(*a*);

FIG. 2(*b*) is a partially enlarged view of FIG. 2(*a*);

PREFERRED EMBODIMENTS FOR CARRYING OUT THE INVENTION

A stem, an inserter, an artificial hip joint system including them, and an artificial hip joint according to an embodiment of the present invention are described in details below with reference to FIGS. 1 to 8. Although the following description is made taking as an example the case of implanting the stem into a left leg, the stem of the present invention can also be implanted into a right leg. The latter is merely in a laterally line-symmetric relationship with the former.

As shown in FIGS. 1 and 2, the artificial hip joint system 20 of the present embodiment includes the stem 1 and the inserter 10.

Figure 8:
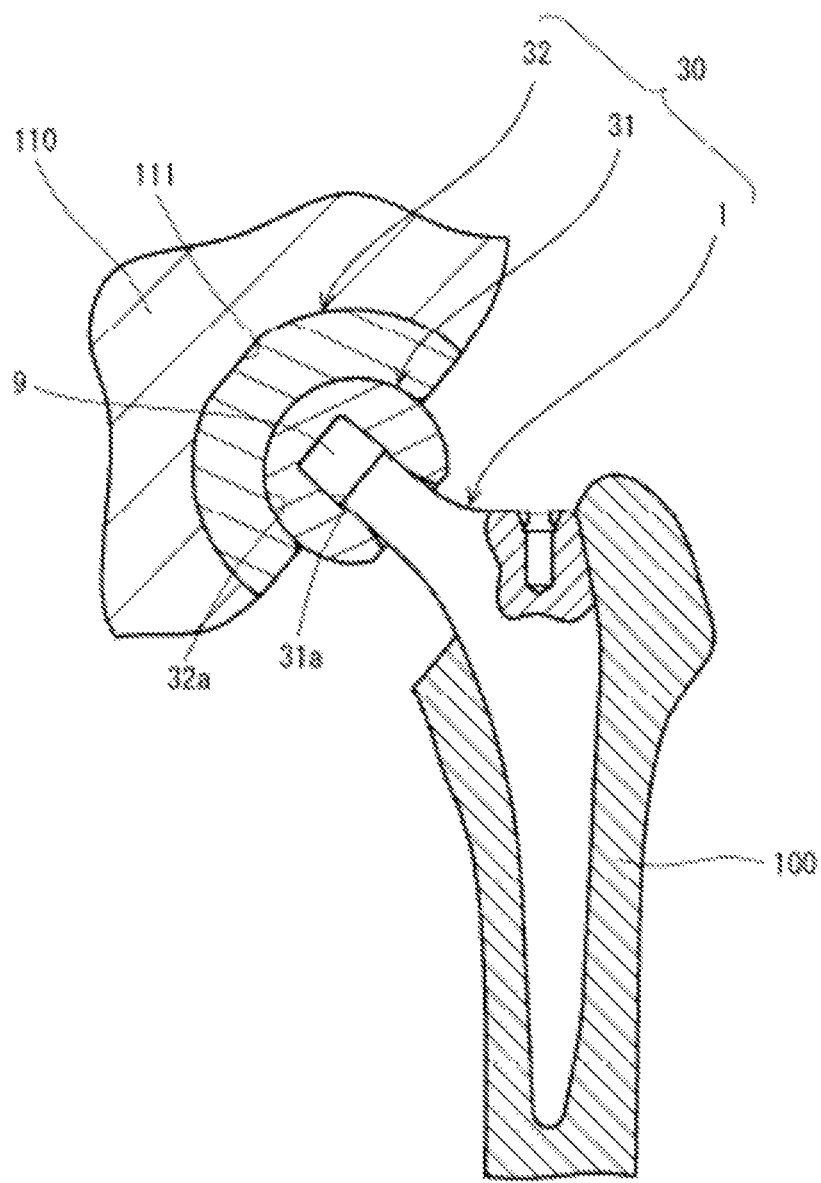
FIG. 8 is a schematic explanatory drawing showing an artificial hip joint according to one embodiment of the present invention.

The stem of the present embodiment is the substantially rod-shaped curved member and constitutes the artificial hip joint 30 by being implanted into a medullary cavity of a thigh bone 100 as shown in FIG. 8. The stem 1 of the present embodiment includes a stem body 2 as shown in FIGS. 4 and 5.

The stem body 2 of the present embodiment is divided into a stem proximal region 2A located in a proximal region and a stem distal region 2B located in a distal region. The phrase "proximal region" denotes the region located closer to the head of a human body than an object to compare upon implantation of the artificial hip joint 30. The phrase "distal region" denotes the region located farther away from the head of the human body than the object to compare upon implantation of the artificial hip joint 30. In other words, the distal region is located closer to the toe tip of the human body.

The stem body 2 of the present embodiment includes a shoulder part 3 located closer to a proximal end and also closer to an outer side in the stem proximal region 2A. The term "outer side" denotes the part located more away from the centerline of the human body than the object to compare upon implantation of the artificial hip joint 30. The term "inner side" described later denotes the part located more closer to the centerline of the human body than the object to compare upon implantation of the artificial hip joint 30.

Figure 3:
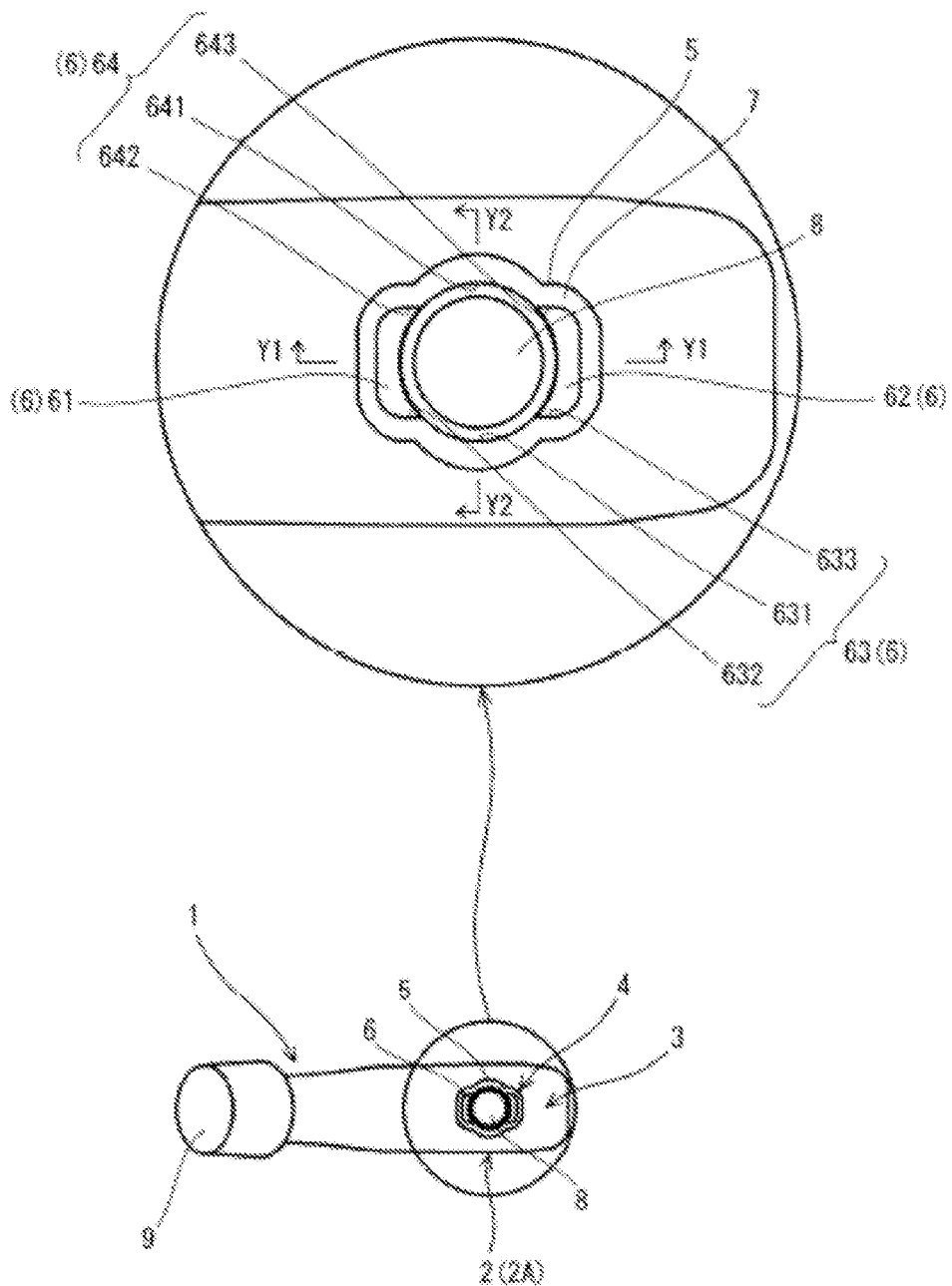
FIG. 3 is an enlarged plan view of an artificial hip joint stem included in the artificial hip joint system shown in FIG. 1 as viewed from an arrowed direction X2 in FIG. 1(*a*)
Figure 4:
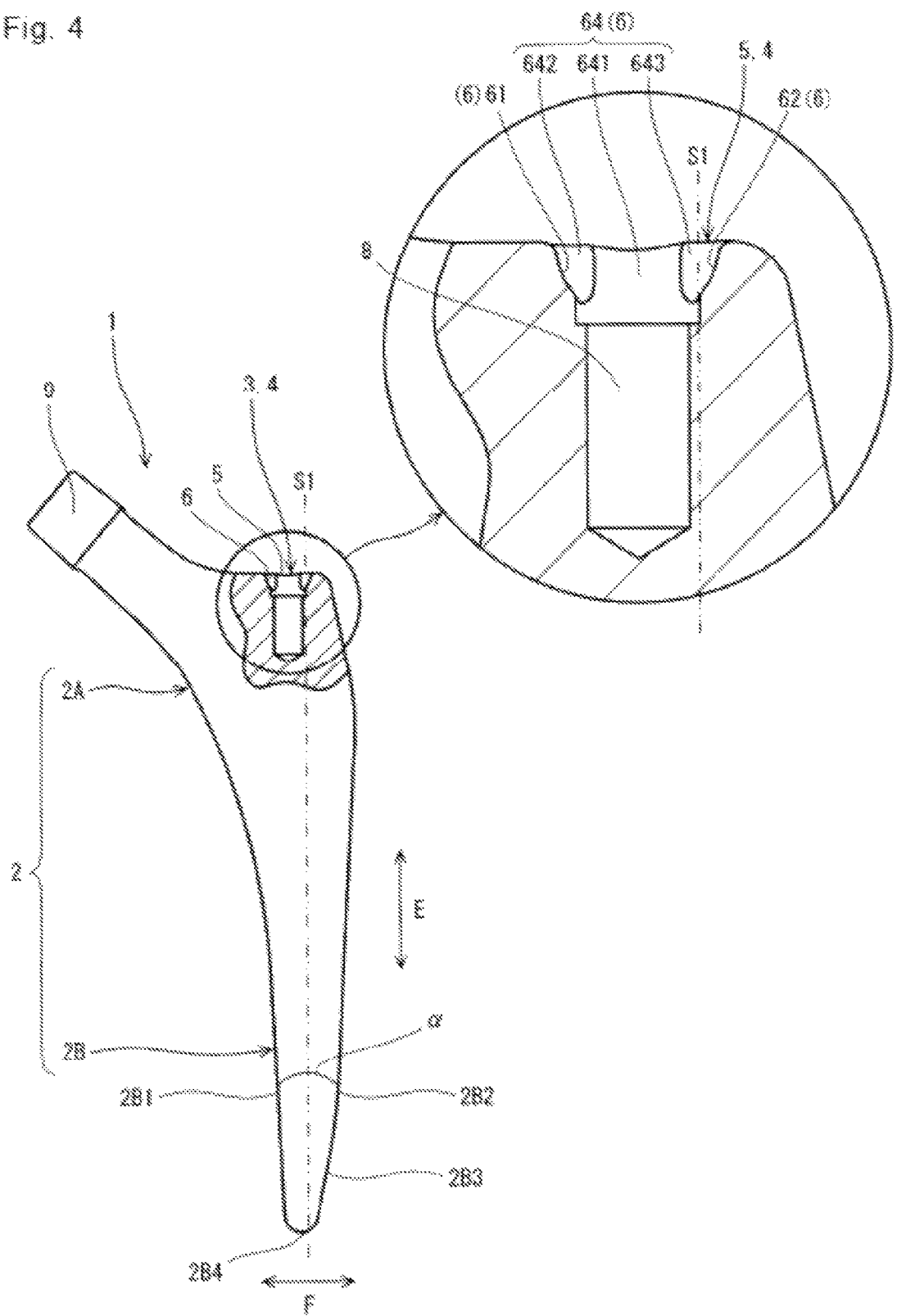
FIG. 4 is an enlarged view of the artificial hip joint stem included in the artificial hip joint system shown in FIG. 1 as viewed from a front side thereof, specifically a cutaway diagram taken along line Y1-Y1 in FIG. 3.
Figure 5:
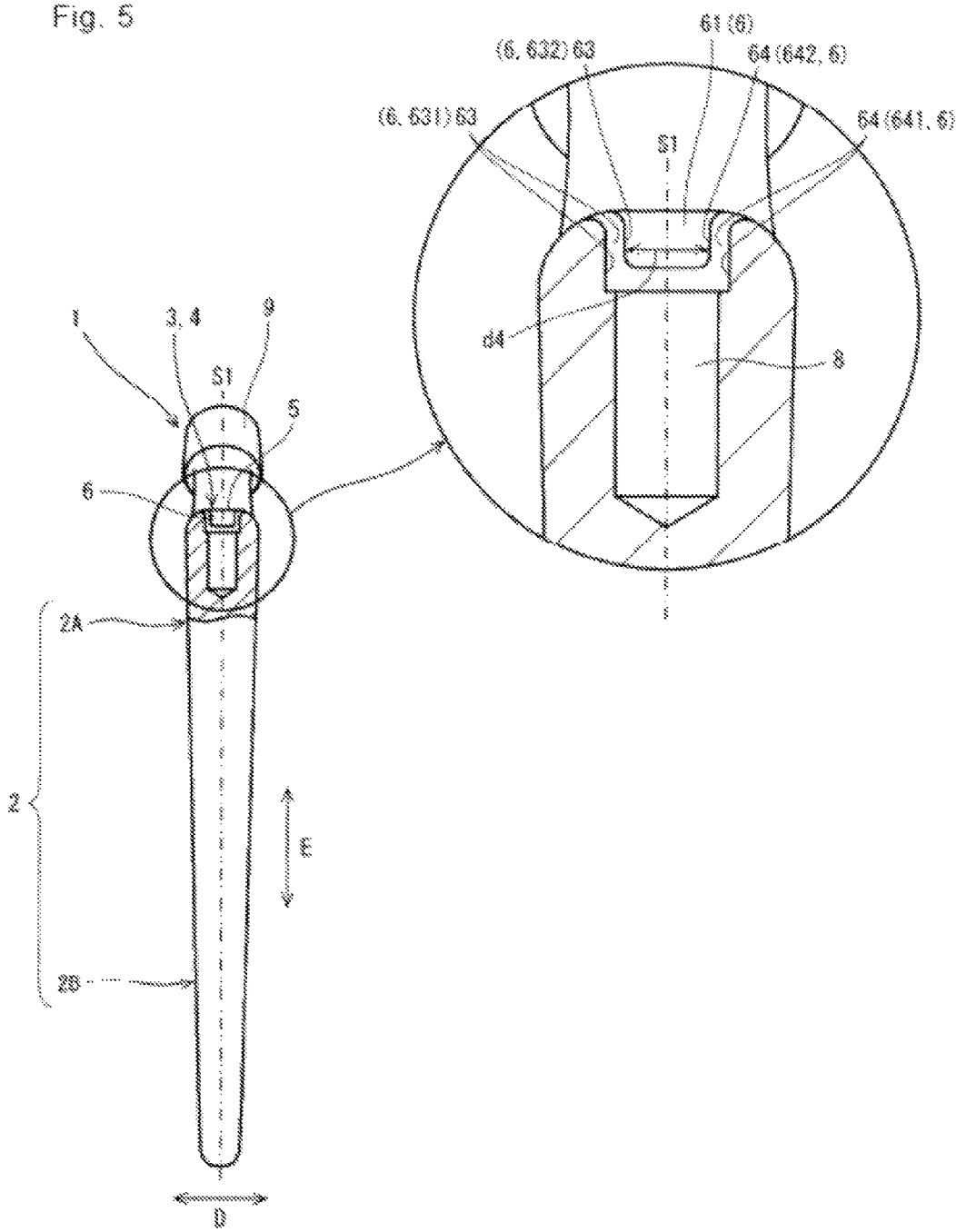
FIG. 5 is an enlarged view of the artificial hip joint stem included in the artificial hip joint system shown in FIG. 1 as viewed from an outer side thereof, specifically a cutaway diagram taken along line Y2-Y2 in FIG. 3.

As shown in FIGS. 3 to 5, the stem 1 of the present embodiment further includes a concave part 4 located in the shoulder part 3. The concave part 4 of the present embodiment includes an opening part 5 that opens into the shoulder part 3, and a wall part 6 extending along a stem central axis S1 of the stem body 2.

As shown in FIG. 5, the stem central axis S1 of the present embodiment is configured so that a midpoint in a thickness direction D in the stem distal region 2B can continuously be obtained along a longitudinal direction E of the stem body 2. As shown in FIG. 4, the stem central axis S1 of the present embodiment is located in the stem distal region 2B and is also a bisector of an angle formed by side surfaces opposed to each other. To be specific, the stem body 2 of the present embodiment further includes an inner side surface 2B1 and an outer side surface 2B2 that are located in the stem distal region 2B. The inner side surface 2B1 is located on an inner side of the stem distal region 2B, and the outer side surface 2B2 is located on an outer side of the stem distal region 2B. In the present embodiment, the inner side surface 2B1 and the outer side surface 2B2 are opposed to each other, and the distance therebetween is decreased as going toward a distal end 2B4 of the stem distal region 2B. Accordingly, the stem central axis S1 of the present embodiment is also the bisector of an angle α formed by the inner side surface 2B1 and the outer side surface 2B2.

When the inner side surface 2B1 and the outer side surface 2B2 are parallel to each other, a configuration with which a midpoint in the width direction F in the stem distal region 2B can continuously be obtained along the longitudinal direction E of the stem body 2 is taken as the stem central axis S1. From the viewpoint of improving implanting performance of the stem 1 with respect to the medullary cavity of the thigh bone 100 in the present embodiment, the outer side surface 2B2 includes an inclined surface 2B3 located closer to the distal end 2B4. When the outer side surface 2B2 includes the inclined surface 2B3 as in the present embodiment, the outer side surface 2B2 used as a basis for determining the stem central axis S1 is one that does not include the inclined surface 2B3.

As shown in FIGS. 3 to 5, the wall part 6 extending along the foregoing stem central axis S1 in the present embodiment includes an inner wall portion 61 and an outer wall portion 62 opposed to each other, and a front wall portion 63 and a rear wall portion 64 opposed to each other. The inner wall portion 61 is located on the inner side of the wall part 6, and the outer wall portion 62 is located on the outer side of the wall part 6. The front wall portion 63 is located on the front side of the wall part 6, and the rear wall portion 64 is located on the rear side of the wall part 6. The phrase "front side" denotes a portion lying along a direction along which the face of the human body is oriented upon implantation of the artificial hip joint 30. The phrase "rear side" denotes a portion lying along a direction along which the back of the human body is oriented upon implantation of the artificial hip joint 30.

In the present embodiment, a distance between the inner wall portion 61 and the outer wall portion 62 is decreased as separating from the opening part 5, in other words, as going toward the distal end of the concave part 4, in a sectional view that is parallel to the stem central axis S1 and includes the inner wall portion 61 and the outer wall portion 62 as shown in FIG. 4.

Also in the present embodiment, both the front wall portion 63 and the rear wall portion 64 have a planar region in a sectional view that is parallel to the stem central axis S1 and includes the front wall portion 63 and the rear wall portion 64 as shown in FIG. 5. In the present embodiment, as shown in FIG. 3, a front inner region 632 and a front outer region 633 included in the front wall portion 63, and a rear inner region 642 and a rear outer region 643 included in the rear wall portion 64 correspond to the planar region.

Figure 6:
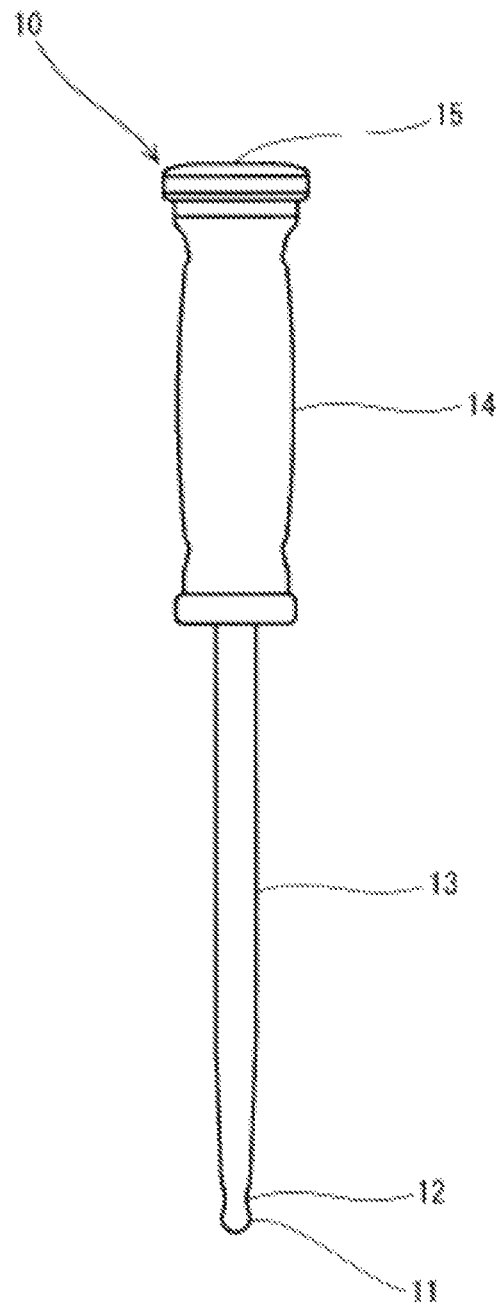
FIG. 6 is a front view showing a stem inserter included in the artificial hip joint system shown in FIG. 1.
Figure 7A:
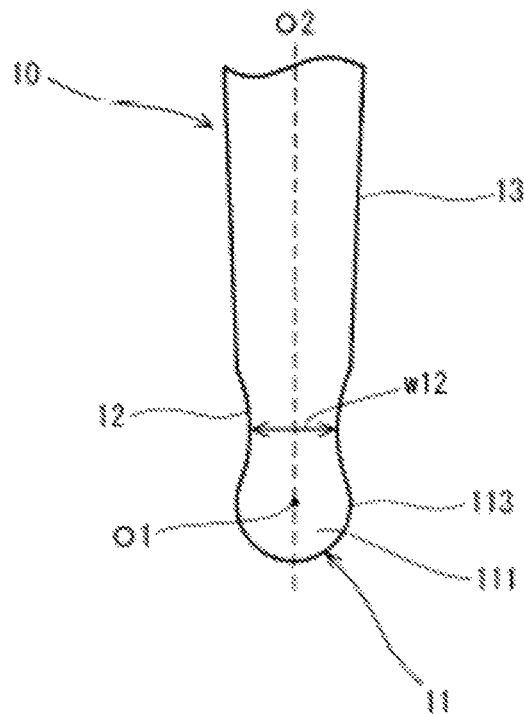
FIG. 7(a) is a partially enlarged front view showing a neighborhood of a front end part of the stem inserter shown in FIG. 6.

On the other hand, the inserter 10 of the present embodiment that constitutes the artificial hip joint system 20 together with the foregoing stem 1 is the member used when the stem 1 is implanted by driving it into the medullary cavity of the thigh bone 100. The inserter 10 of the present embodiment includes a substantially disk-shaped front end part 11 as shown in FIGS. 6 and 7.

The front end part 11 of the present embodiment is at least partially housed in the foregoing concave part 4, and has a shape corresponding to the concave part 4. To be specific, the front end part 11 includes a planar upper surface 111, a planar lower surface 112, and a curved surface-shaped side surface 113 connected to each of the upper surface 111 and the lower surface 112 as shown in FIG. 7. In the present embodiment, the upper surface 111 and the lower surface 112 are identical in size, and the front end part 11 has a thickness d11 that is somewhat smaller than a distance d4 of the concave part 4 shown in FIG. 5. The distance d4 is the distance between the planar region in the front wall portion 63 (front inner region 632) and the planar region in the rear wall portion 64 (rear inner region 642).

Figure 1A:
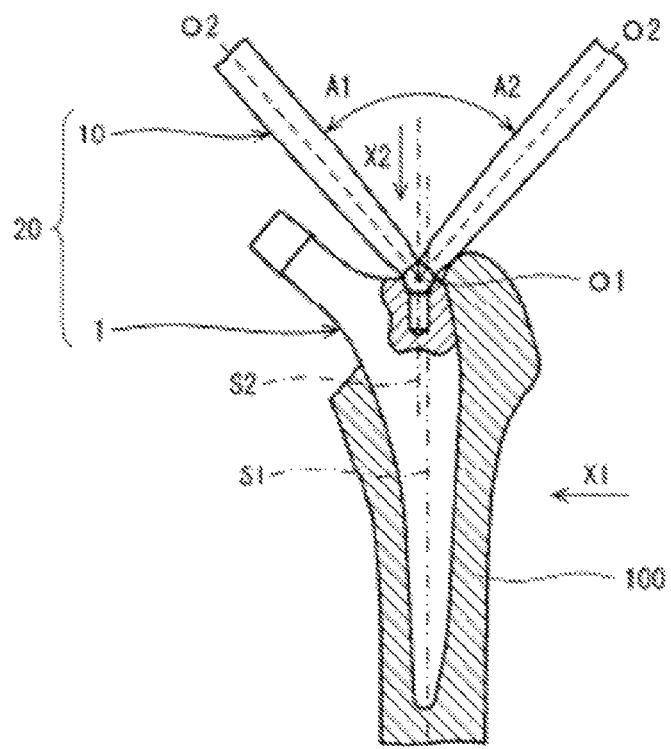
FIG. 1(*a*) is a schematic explanatory drawing of an artificial hip joint system according to an embodiment of the present invention as viewed from a front side thereof.
Figure 1B:
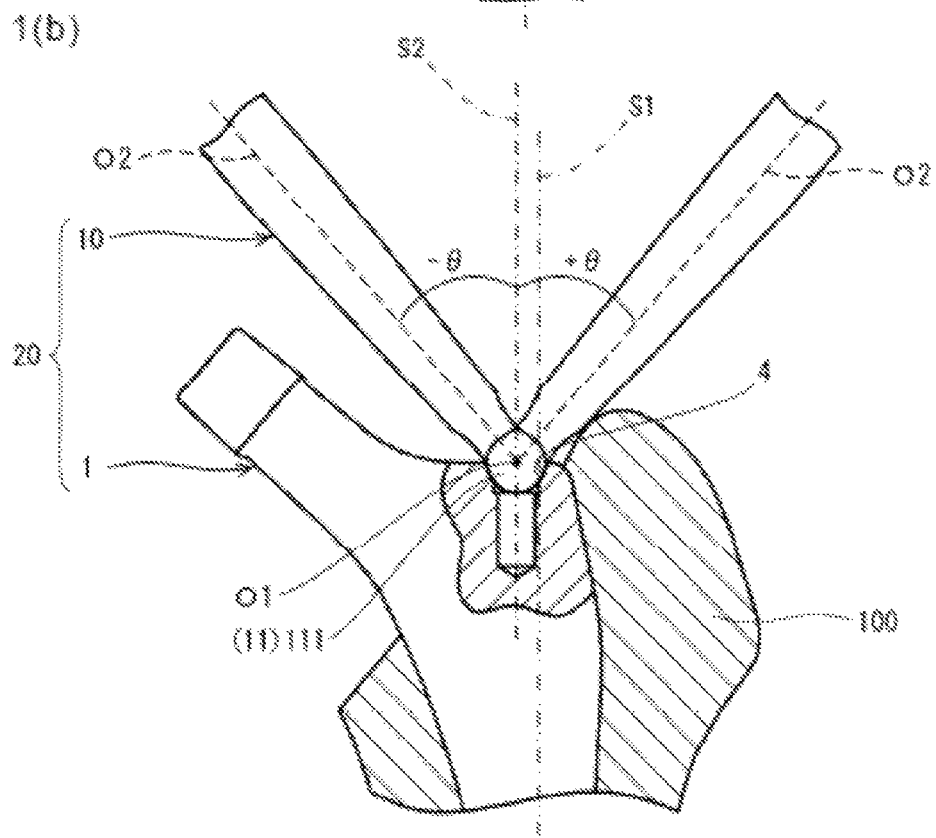
Figure 2A:
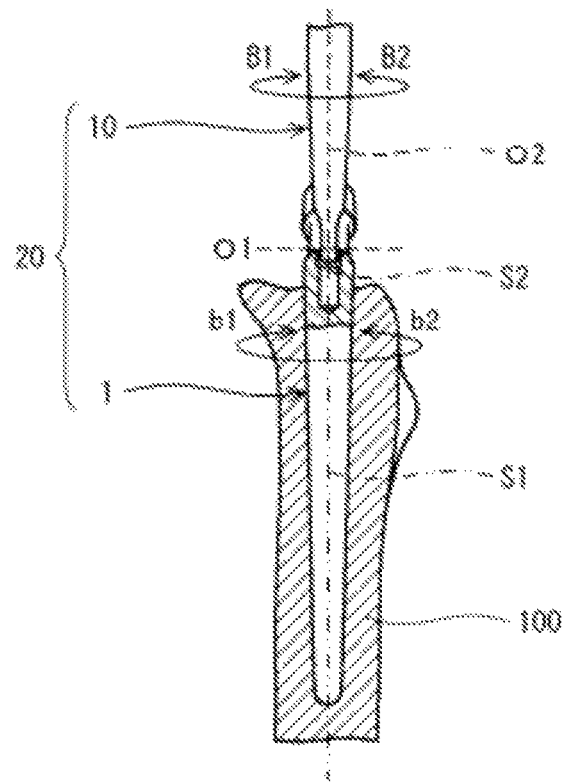
FIG. 2(*a*) is a schematic explanatory drawing of the artificial hip joint system shown in FIG. 1, as viewed from an arrowed direction X1 in FIG. 1(*a*)
Figure 2B:
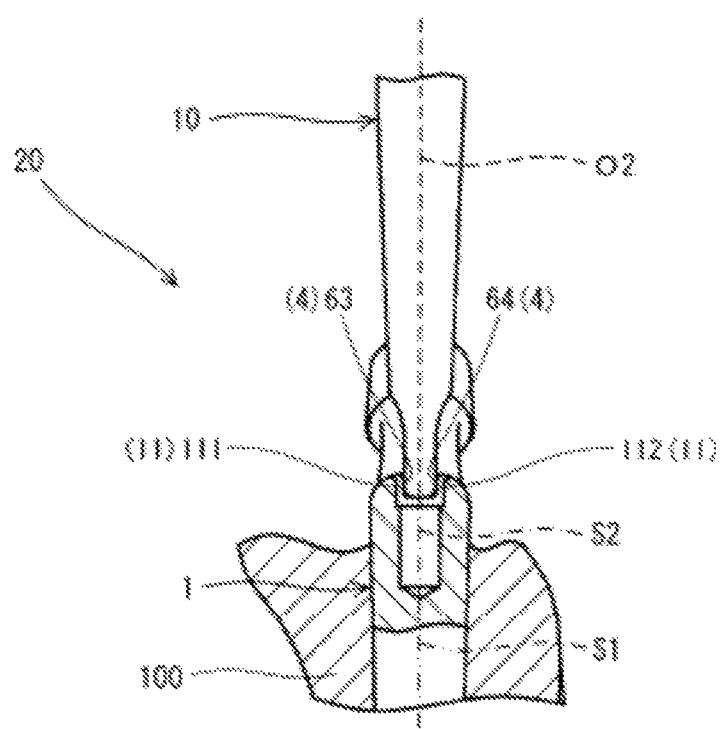

As shown in FIG. 2(b), the inserter 10 of the present embodiment is housed in the concave part 4 in a state that the upper surface 111 and the lower surface 112 of the front end part 11 are respectively opposed to the front wall portion 63 and the rear wall portion 64 of the concave part 4. As shown in FIG. 1(b), the inserter 10 of the present embodiment is also housed in the concave part 4 so as to be inclinable around an inserter central axis O1 extending between the upper surface 111 and the lower surface 112. These configurations ensure excellent driving performance described below.

That is, the distance between the inner wall portion 61 and the outer wall portion 62 of the concave part 4 is decreased as separating from the opening part 5 as described above in the present embodiment. Therefore, at the time the inserter 10 is housed in the concave part 4 in the foregoing positional relationship, the inserter 10 is inclinable in arrowed directions A1 and A2 around the inserter central axis O1 as shown in FIG. 1(a). Hence according to the present embodiment, when driving the stem 1 into the medullary cavity of the thigh bone 100, it is capable of driving the stem 1 from different angles by freely inclining the inserter 10 in the arrowed directions A1 and A2 around the inserter central axis O1. This contributes to reducing the biting between the stem 1 and the inserter 10, as well as difficulty in removing the two. This also contributes to reducing damage to the stem 1 and the inserter 10. Additionally, even when a driving angle is changed during the implantation of the stem 1, it is capable of driving the stem 1 while controlling a driving angle by inclining the inserter 10.

Further in the present embodiment, both the front wall portion 63 and the rear wall portion 64 of the concave part 4 have the planar region as described above. Therefore, when the inserter 10 is rotated in arrowed directions B1 and B2 around an inserter rotation axis O2 perpendicular to the inserter central axis O1 as shown in FIG. 2(a), the upper surface 111 and the lower surface 112 are brought into contact with the front wall portion 63 and the rear wall portion 64, and consequently the stem 1 is rotatable in arrowed directions b1 and b2. Hence, according to the present embodiment, it is capable of driving the stem 1 while adjusting the rotation angle of the stem 1.

Figure 7B:
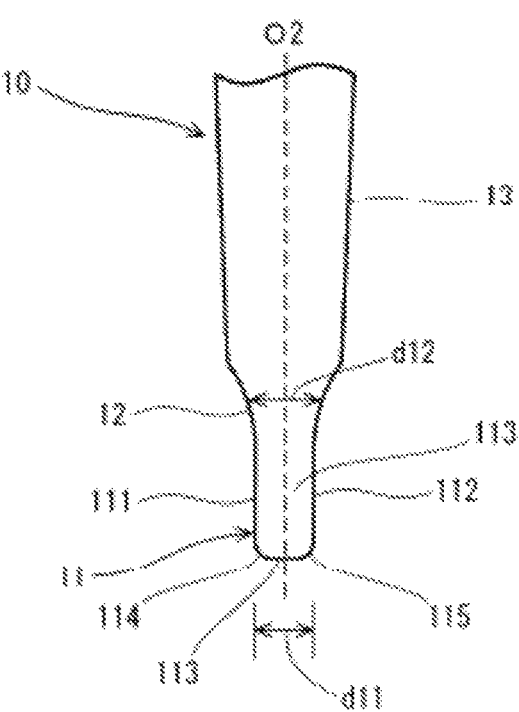
FIG. 7(b) is a partially enlarged side view thereof.

From the viewpoint of improving housing performance of the inserter 10 into the concave part 4 in the present embodiment, the front end part 11 of the inserter 10 further includes an upper chamfered portion 114 formed by chamfering the intersection of the upper surface 111 and the side surface 113 as shown in FIG. 7(b). Similarly, the front end part 11 includes a lower chamfered portion 115 formed by chamfering the intersection of the lower surface 112 and the side surface 113.

The inserter 10 of the present embodiment further includes a connection part 12, a column-shaped shaft 13, a grip 14 and a top plate 15, which are disposed sequentially from the front end part 11 as shown in FIG. 6.

The connection part 12 of the present embodiment is connected to each of the front end part 11 and the shaft 13, and both a width w12 and a thickness d12 of the connection part 12 are increased as going from the front end part 11 to the shaft 13 as shown in FIG. 7. This configuration contributes to setting a large inclination angle θ of the inserter 10 described later.

In the present embodiment, as shown in FIG. 1(b), the inclination angle θ of the inserter 10 is ±35 to 45° in a front view of the inserter 10. This configuration contributes to increasing the inclination angle θ of the inserter 10 and also makes it easier for force applied when driving the stem 1 to be transmitted to the stem 1.

The phrase "front view of the inserter 10" denotes a state that the inserter 10 is viewed from the upper surface 111 of the front end part 11. The phrase "inclination angle δ of the inserter 10" denotes an angle formed by the inserter rotation axis O2 and the stem central axis S1 or a reference line S2 parallel to the stem central axis S1. In the present embodiment, the angle formed by the inserter rotation axis O2 and the reference line S2 is the inclination angle θ of the inserter 10. In terms of the inclination angle θ of the inserter 10, an angle formed outside the stem central axis S1 or the reference line S2 is determined as being plus (+), and an angle formed inside the stem central axis S1 or the reference line S2 is determined as being minus (−).

In the inserter 10 of the present embodiment, the front end part 11, the connection part 12 and the shaft 13 are integrally molded. No specific limitation is imposed on materials constituting the front end part 11, the connection part 12 and the shaft 13 as long as they are materials having resistance to sterilization treatment for medical devices, such as gamma sterilization. In the inserter 10 of the present embodiment, the grip 14 is gripped by an operator, and the top plate 15 is struck by a hammer.

Whereas in the present embodiment, both the inner wall portion 61 and the outer wall portion 62 of the concave part 4 are formed in an arc-shaped curved surface as shown in FIG. 4. That is, both the inner wall portion 61 and the outer wall portion 62 have an arc shape in the sectional view that is parallel to the stem central axis S1 and includes the inner wall portion 61 and the outer wall portion 62. This configuration contributes to setting the large inclination angle θ of the inserter 10 while ensuring strength of a neck part 9 described later.

Additionally in the present embodiment, as shown in FIG. 5, the front wall portion 63 and the rear portion 64 are parallel to each other in the sectional view that is parallel to the stem central axis S1 and includes the front wall portion 63 and the rear wall portion 64. This configuration allows the inserter 10 to be smoothly inclined around the inserter central axis O1.

In the present embodiment, the front wall portion 63 further includes a front groove 631 extending along the stem central axis S1 as shown in FIGS. 3 and 5. The front inner region 632 and the front outer region 633 are spaced away from each other with the front groove 631 interposed therebetween. Similarly, the rear wall portion 64 further includes a rear groove 641 extending along the stem central axis S1. The rear inner region 642 and the rear outer region 643 are spaced away from each other with the rear groove 641 interposed therebetween. The front groove 631 is located in a substantially central region made up of the front wall portion 63, and the rear groove 641 is located in a substantially central region of the rear wall portion 64. The inserter 10 can be held by the four surfaces of the front inner region 632, the front outer region 633, the rear inner region 642 and the rear outer region 643.

The concave part 4 further includes a chamfered portion 7 formed by chamfering an edge of the wall part 6 located closer the opening part 5 in the present embodiment as shown in FIG. 3. This configuration improves the housing performance of the inserter 10 into the concave part 4. The chamfered portion 7 of the present embodiment lies over the entire circumference of the opening part 5.

As shown in FIGS. 1(b) and 2(b), the concave part 4 is partially located on the stem central axis S1 in the present embodiment. This configuration facilitates the transmission of the force applied when driving the stem 1.

As shown in FIGS. 3 to 5, the concave part 4 further includes a screw hole 8 located closer to the distal end of the concave part 4 in the present embodiment. The screw hole 8 is fixable by a screw to a screw part located at the front end of the foregoing conventional inserter. Therefore, the stem 1 of the present embodiment can be driven by using the conventional inserter as necessary. The stem 1 can also be removed by using the conventional inserter.

The stem 1 of the present embodiment further includes the neck part 9 extending from the proximal end of the stem body 2. Examples of materials constituting the stem 1 are titanium alloy and cobalt-chrome alloy.

As described above, the stem 1 of the present embodiment constitutes the artificial hip joint 30 shown in FIG. 8. The artificial hip joint 30 of the present embodiment includes, besides the foregoing stem 1, an artificial bone head 31 fitted into the neck part 9 of the stem 1, and a socket 32 that slidably houses the artificial bone head 32 and is fixed to an acetabulum 111 of a coxa 110.

The artificial bone head 31 of the present embodiment has a substantially spherical shape and includes a bottomed cylinder-shaped concave part 31a located in a bottom central region thereof. The artificial bone head 31 is fitted into the neck part 9 of the stem 1 with the concave part 31a interposed therebetween. Examples of materials constituting the artificial bone head 31 are metals, such as cobalt-chrome alloy, and ceramics, such as alumina and zirconia.

The socket 32 of the present embodiment is substantially cup shaped and includes a substantially semispherical-shaped concave part 32a located in a bottom central region thereof. The socket 32 slidably houses the artificial bone head 31 in the concave part 32a. Examples of materials constituting the socket 32 are synthetic resins, such as polyethylene resin.

While the embodiment of the present invention has been illustrated and described, it is to be understood that the present invention is not limited to the foregoing embodiment, but many modifications and changes can be made without departing from the spirit and scope of the present invention.

Figure 9:
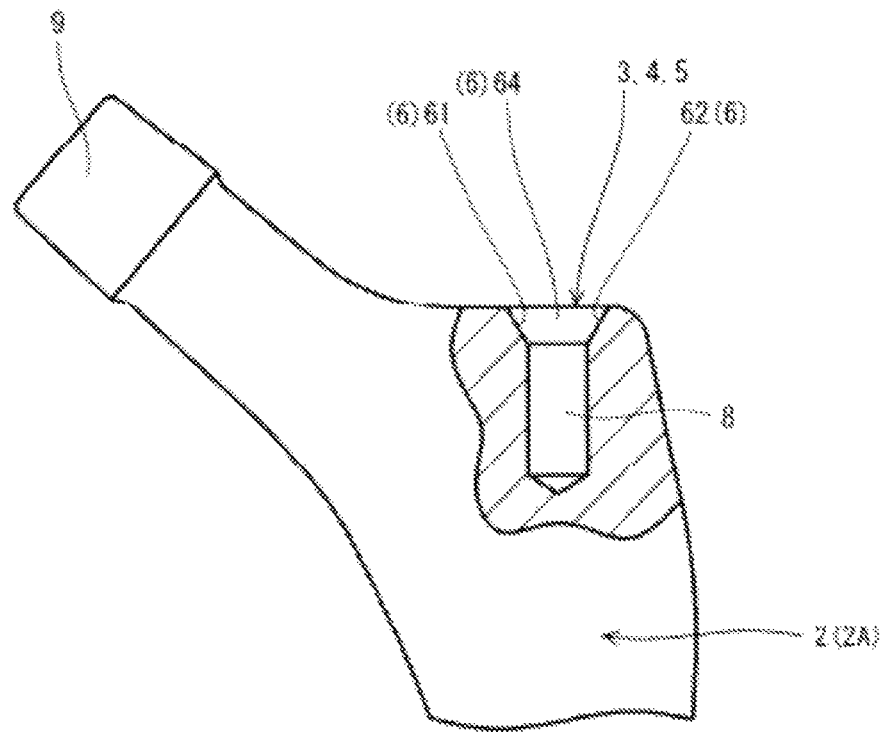
FIG. 9 is a partially enlarged schematic explanatory drawing of an artificial hip joint stem according to other embodiment of the present invention, as viewed from a front side thereof, FIG. 9 being equivalent to FIG. 4.

For example, according to the foregoing embodiment, both the inner wall portion 61 and the outer wall portion 62 of the concave part 4 have the arc shape in the sectional view that is parallel to the stem central axis S1 and includes the inner wall portion 61 and the outer wall portion 62. Alternatively, the inner wall portion 61 and the outer wall portion 62 may be made into a structure as shown in FIG. 9. That is, as shown in FIG. 9, both the inner wall portion 61 and the outer wall portion 62 may have a tapered shape. In other words, both the inner wall portion 61 and the outer wall portion 62 may be comprised of an inclined surface. This configuration simplifies the structure of the concave part 4, thereby improving productivity of the stem 1. Additionally, the size of the front end part 11 in the inserter 10 is freely changeable as long as the front end part 11 can be housed in the concave part 4.

According to the foregoing embodiment, the front wall portion 63 includes the front groove 631 and the rear wall portion 64 includes the rear groove 641. Alternatively, the front wall portion 63 may not include the front groove 631, and a substantially entire surface of the front groove 631 may include a planar region. The rear wall portion 64 may not include the rear groove 641, and a substantially entire surface of the rear wall portion 64 may include a planar region.

Figure 10:
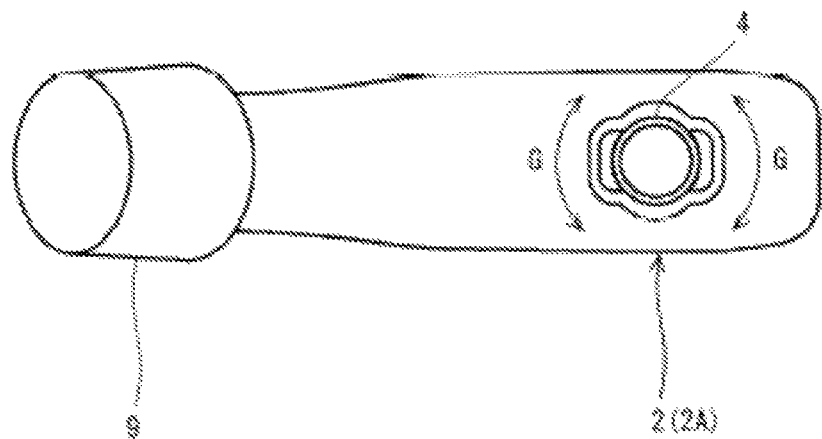
FIG. 10 is an enlarged plan view showing an artificial hip joint stem according to still other embodiment of the present invention.

As an alternative to the foregoing embodiment, the position of the concave part 4 may be adjusted in an arrowed direction G as long as the strength of the stem body 2 can be maintained, as shown in FIG. 10.

What is claimed is:

1. An artificial hip joint stem, comprising:
a concave part located in a shoulder part of a stem body, the concave part comprising:
an opening part that opens into the shoulder part, and
a wall part extending along a stem central axis of the stem body,
the wall part comprising:
an inner wall portion and an outer wall portion opposed to each other, and
a front wall portion and a rear wall portion opposed to each other,
wherein a distance between the inner wall portion and the outer wall portion decreases going toward a distal end of the concave part from the opening part in a sectional view that is parallel to the stem central axis and includes the inner wall portion and the outer wall portion, and the distance between the inner wall portion and the outer wall portion begins to decrease at a location closer to the opening part of the concave part than the distal end of the concave part, and
both the front wall portion and the rear wall portion have a planar region in a sectional view that is parallel to the stem central axis and includes the front wall portion and the rear wall portion, and
the front wall portion comprises a front groove extending along the stem central axis and the rear wall portion comprises a rear groove extending along the stem central axis.

2. The artificial hip joint stem according to claim 1, wherein both the inner wall portion and the outer wall portion have an arc shape or tapered shape in the sectional view that is parallel to the stem central axis and includes the inner wall portion and the outer wall portion.

3. The artificial hip joint stem according to claim 1, wherein both the front wall portion and the rear wall portion are parallel to each other in the sectional view that is parallel to the stem central axis and includes the front wall portion and the rear wall portion.

4. The artificial hip joint stem according to claim 1, wherein the front wall portion comprises:
a front inner region and a front outer region spaced away from each other with the front groove interposed therebetween; and
the rear wall portion comprises:
a rear inner region and a rear outer region spaced away from each other with the rear groove interposed therebetween.

5. The artificial hip joint stem according to claim 4, wherein the front groove is located in a central region of the front wall portion, and the rear groove is located in a central region of the rear wall portion.

6. The artificial hip joint stem according to claim 1, wherein the concave part further comprises a chamfered portion formed by chamfering an edge portion of the wall part located closer to the opening part.

7. The artificial hip joint stem according to claim 1, wherein the concave part is partially located on the stem central axis.

8. The artificial hip joint stem according to claim 1, wherein the concave part further comprises a screw hole located closer to a distal end of the concave part.

9. The artificial hip joint stem according to claim 1, further comprising: a neck part extending from a proximal end of the stem body.

10. An artificial hip joint system, comprising an artificial hip joint stem according to claim 1 and a stem inserter comprising:
a disk-shaped front end part having a planar first surface, a planar second surface, and a curved surface shaped side surface connected to each of the planar first surface and the planar second surface;
a column-shaped shaft; and
a connection part connected to each of the front end part and the shaft,
wherein an inserter central axis extending between the planar first surface and the planar second surface is vertical with respect to an inserter rotation axis extending along a longitudinal direction of the shaft, and
the stem inserter is housed in the concave part of the stem in a state that the planar first surface and the planar second surface of the front end part are respectively opposed to the front wall portion and the rear wall portion of the concave part of the stem, and in a state that the stem inserter is inclinable around the inserter central axis.

11. The artificial hip joint system according to claim 10, wherein the stem inserter has an inclination angle of ±35 to 45° in a front view of the stem inserter.

12. An artificial hip joint, comprising an artificial hip joint stem according to claim 9, an artificial bone head fitted into the neck part, and a socket for slidably housing the artificial bone head.

13. The artificial hip joint system according to claim 10, wherein the front end part of the stem inserter further comprises a first chamfered portion formed by chamfering an intersection of the planar first surface and the side surface, and a second chamfered portion formed by chamfering an intersection of the planar second surface and the side surface.

14. The artificial hip joint system according to claim 10, wherein the connection part of the stem inserter comprises a width and a thickness, each of the width of the connection part and the thickness of the connection part increases from the front end part to the shaft.

15. The artificial hip joint stem according to claim 1, wherein the inner wall portion and the outer wall portion are non-threaded.

16. The artificial hip joint system according to claim 10, wherein the inner wall portion and the outer wall portion are non-threaded.

\* \* \* \* \*